United States Patent [19]

Varone

[11] Patent Number: 4,538,107
[45] Date of Patent: Aug. 27, 1985

[54] CABLE FAILURE DETECTION SYSTEM

[76] Inventor: Richard B. Varone, 81 Hilltop Dr., Smithtown, N.Y. 11787

[21] Appl. No.: 456,544

[22] Filed: Jan. 10, 1983

[51] Int. Cl.³ .............................................. G01B 7/04
[52] U.S. Cl. ..................................... 324/206; 324/51; 324/242
[58] Field of Search ................. 324/206, 240, 242, 51, 324/52, 228, 239

[56] References Cited

U.S. PATENT DOCUMENTS

| 2,970,256 | 1/1961 | Sazynski et al. | 324/240 |
| 3,555,412 | 1/1971 | Fowler | 324/228 |
| 4,335,352 | 6/1982 | Stephen | 324/239 X |
| 4,427,940 | 1/1984 | Hirama et al. | 324/206 X |
| 4,445,088 | 4/1984 | Schubel | 324/240 X |

FOREIGN PATENT DOCUMENTS

| 1533 | 1/1980 | Japan | 324/206 |
| 63756 | 5/1980 | Japan | 324/240 |
| 114947 | 9/1980 | Japan | 324/240 |
| 2067766 | 7/1981 | United Kingdom | 324/240 |

Primary Examiner—Stanley T. Krawczewicz
Attorney, Agent, or Firm—Leonard Belkin

[57] ABSTRACT

A cable failure detection system is provided that detects changes in the magnetic field of a cable that has been magnetized said changes in the magnetic field coming about due to a flaw in said cable. Said changes are sensed by a gauss meter which generates a signal, said signal being converted into a visual or audio signal for early warning of failure.

5 Claims, 3 Drawing Figures

CABLE FAILURE DETECTION SYSTEM

BACKGROUND OF THE INVENTION

1. Field of Invention

The cable failure detection system is an apparatus and method to detect cable failure.

The instant invention relates generally to cable failure detection and specifically said invention will detect a small break, wear, fraying or any other type of cable flaw in a magnetized cable and said system will activate a sensing means so that corrective measures may be taken to prevent the small break, wear, fraying or any other type of cable flaw from not materializing into a complete cable failure.

2. Description of the Prior Art

The prior art is void of any simple low cost effective means to detect cable damage which ultimately may lead to cable failure and accordingly the instant invention provides such a system.

SUMMARY OF THE INVENTION

This invention detects change in the magnetic field of a magnetized cable or cables due to an inconsistancy or fault in said magnetized cable or cables. Said magnetic change is sensed by a gauss meter which generates a signal to an electronic detection device which in turn converts said signal into a visual and/or audio signal so that the inconsistancy or fault in said cable becomes apparent.

The instant cable failure detection system is to aid in the safety of the public and aid in the manufacturing of new cables to insure that said cables have been manufactured without flaws or defects.

Said cable failure detection system may be easily adaptable for use on all ferrous or magnetizable types of metal cables and by the use of magnetism said detection system can detect any single or multiple strand break or damage in addition to wear, fraying, etc. and may be used on any type of cables so long as said cables have magnetizable capabilities. Said cable failure detection system is directed for use to insure the safety of people and typical installations would be for use on ski lifts, elevators, tramways, cable cars, window washer cables used on skyscrapers, etc. Said failure detection system may also be used at cabling manufacturing plants as a quality control device to inspect manufactured cables.

The cable failure detection system operates with magnetism and electronic equipment by means of magnetizing the cable prior to its encounter with a magnetic sensing device said magnetic sensing device being commonly known throughout the industry as a gauss meter/detector or magnetometer. In operation the cable is magnetized by being passed through a magnetic field thereby creating lines of flux around the magnetized portion of the cable which is created by the magnets. The cable then moves past the magnetic sensing device which scans said cable and its lines of flux and detects whether any lines of magnetic flux have changed its state or conditions. After the cable passes through said magnetic field, the magnetized states of the cable will be in one of the two following conditions (a) when there are no breaks or damages in the cables, the logical state of the lines of flux are equal to "zero"; and (b) when there is a definite break or damage in the cable the lines of flux changes its state from a "zero" condition to a "1" condition. Said magnetic sensing device generates a signal. When said signal stays in a uniformed type of fashion, the cable is considered in a zero or a low state. When the magnetic sensing device generates a signal with a spike or spikes (be it, that the spike is going high in a positive (+) upward area or low on a negative (−) downward area), this represents a "1" condition or high state. It is the state of the cable's conditions that determines said "zero" or "1" state, that is, if there is no breakage or damage of a single strand or strands a low or zero condition exists. If there is a breakage or signs of damage (i.e. wear, fraying, etc.) of a single strand or strands, a high or "1" state exists.

The magnetic sensing device senses these patterns of "zeros" or lows (no breaks or no damages) and "1" or highs (with breaks or damages) and when said magnetic sensing device has detected the breaks or damages it generates a positive (+) or negative (−) pulse on its electronic signal path. Said pulse is communicated from the magnetic sensing device to electronical equipment which is designed for signal rejuvenations, amplifications, filtering, triggering of electronic gates, relays, and finally sounding of an alarm or other informative type of equipment.

The aforementioned system may also be used as a portable cable scanning device (manual or automatic) or a centralized computer scanning device for an entire network of elevators, ski lifts, etc.

DETAILED DESCRIPTION OF THE PREFERRED EMBODIMENTS

Figure 1:
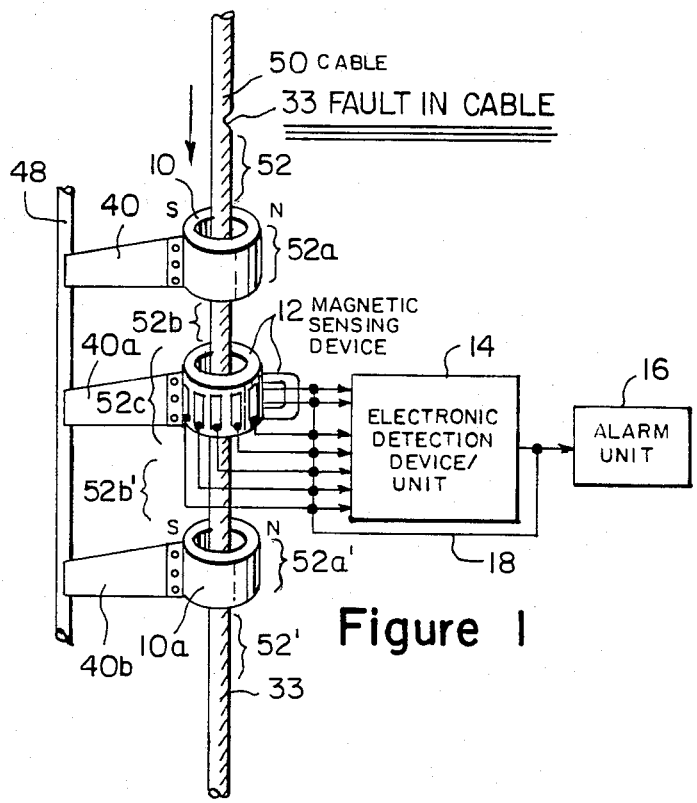
FIG. 1 is a schematic illustration of a preferred embodiment of the invention.

The cable failure detection system consists of four (4) components: (Components 2, 3 and 4 use power supplies)

1. Magnets and their different shapes with their supporting brackets (10, 10a, 40 and 40b).
2. Magnetic sensing devices and their different shapes with their supporting brackets (12 and 40a).
3. Electronic detection device/unit (14).
4. Alarm unit (16).

Referring to FIG. 1, magnets 10 and 10a are provided and are sized and oriented according to the requirements of a particular use such as for ski lifts, elevators, tramways, skyscraper window washers' cable, cable cars for amusement parks, etc. said magnets being held in place by supporting brackets 40 and 40b. Sensing device 12 is provided with supporting brackets and the electronic detection device 14 is typically located near said magnetic sensing device 12 or may be located in a monitoring room or where elevators, ski lifts, etc. would be monitored depending upon the need of the users.

For cable runs in excess of 50 feet from the magnetic sensing device 12 or the electronic detection unit 14 a line repeater device would be used between those units 12 and 14 and their terminating points. Line repeaters amplify the signal/s to prevent deterioration of signals being sent via cable from one unit to another. Line repeaters are a common device used throughout the electronic industry for the transmission of electronic signals. Fiber optic components and cable would also be used in the transmission of the signals from component 12 to components 14 and 16 said fiber optic equipment being standard in the industry.

FIG. 1 indicates the cable failure detection system in an operating condition. Brackets 40, 40a and 40b are provided for holding the magnets and magnetic sensing device and are attached to support 48 such as a wall or steel girder and the magnetizable or ferrous type cable 50 passes through or under the magnets 10. On cable 50 there exists an area with a broken or damaged strand or strands (fault point) 33 on or in the cable and said cable 50 enters area 52 which is the area of cable before entering through or past magnets 10. Cable 50 then enters area 52a which is the area of cable passing under or through said magnets 10 and said cable is the area 52a then becomes magnetized. After cable 50 leaves the magnetic field 52a, said cable enters area 52b which is the area of cable which passed under or through the magnet 10 and accordingly has become magnetized. Fault point 33, which passed by magnets 10, now leaves the magnet area 10 in a magnetized state and is directed into the magnetic sensing area 52c which consists of one or more gauss meters with the cable being continuously scanned by said gauss meters and as the magnetized area of the cable on either side of fault point 33 passes under or through the magnetic sensing device 12, the signal perceived by magnetic sensing device 12 is normal since magnetic sensing device 12 as of yet has not sensed the fault point 33 which is the broken or damaged strand or strands of cable 50. Said magnetic sensing device 12 detects the fault area 33, as fault point 33 passes through said magnetic sensing device 12 and generates a signal to the electronic detection device 14, and said electronic detection device 14 sends a signal to remote alarm unit 16 thereby, triggering and audiable alarm with the signals being transmitted on conductive line 18.

Magnetic sensing device 12 is capable of sensing in either direction and accordingly it enables the positioning of a second magnet 10a on the opposite side of the magnetic sensing device's first magnet 10 for bi-directional scanning.

Figure 2:
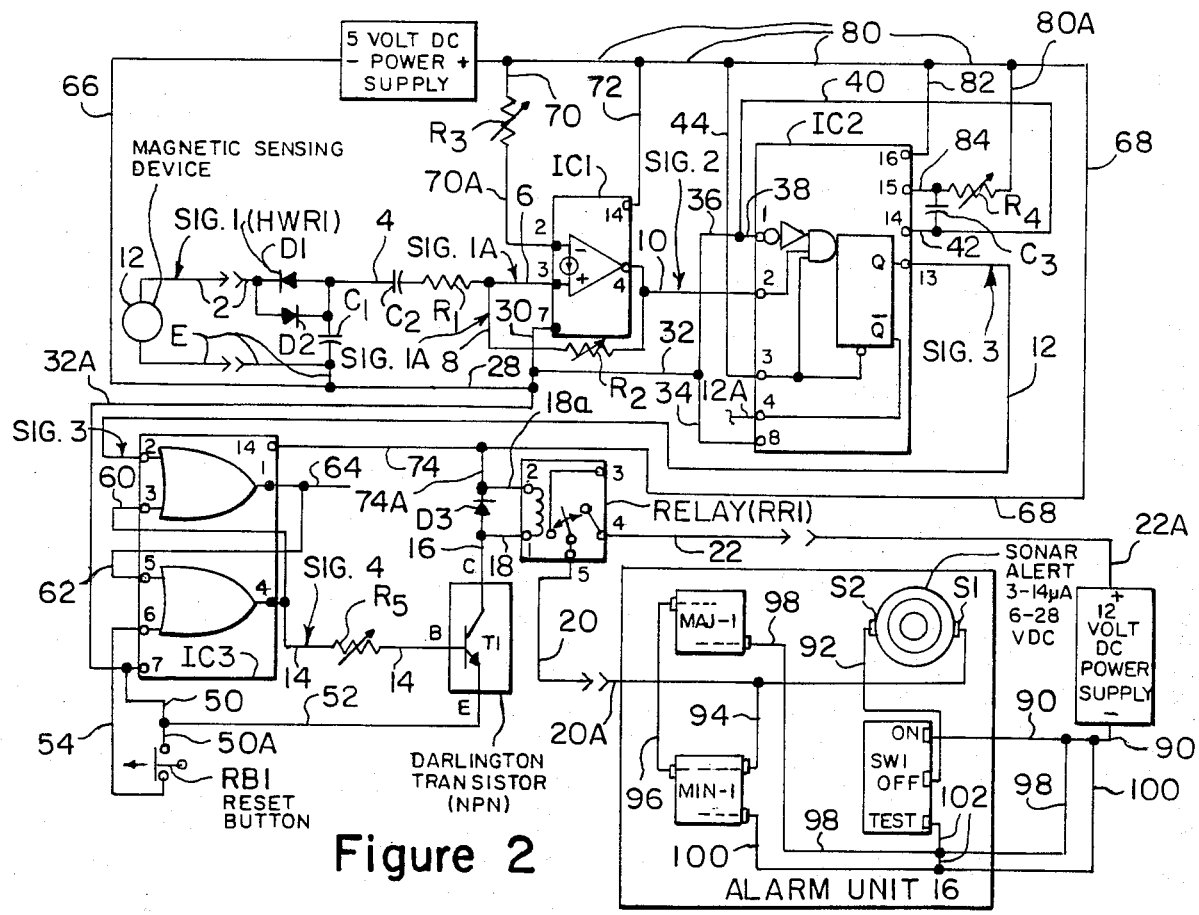
FIG. 2 shows details of the electronic circuitry for the apparatus shown in FIG. 1.

Referring to FIG. 2, a signal flows from the magnetic sensing device 12 through the electronic detection device 14 to alarm unit 16. Said electronic detection device 14 receives signals from the magnetic sensing device 12 which have been generated by the detection of a broken or damaged cable strand or strands and converts said signals into useable signals.

Figure 1A:
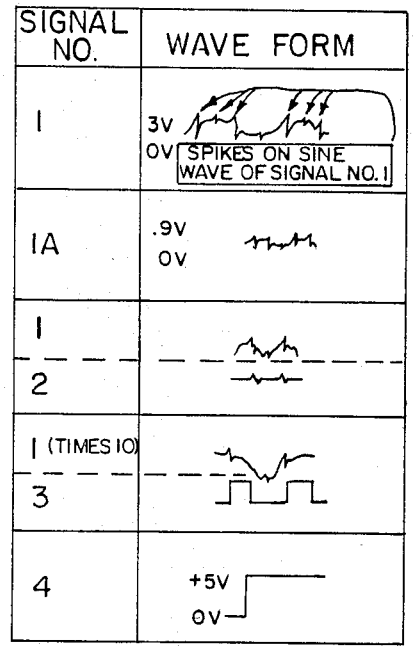
FIG. 1A is a waveform diagram for the apparatus shown in FIG. 1.

The output signal of magnetic sensing device 12 is a sine wave with spikes (site signal 1) which is generated from the detection of the magnetized cables. The spikes on signal 1 of said sine wave increase if a break or damage (fault) of a strand or strands are detected and said signal travels through conductive line 2 to a halfwave rectifier HWR1 (site D1,D2 configuration) filtered by a capacitor C1 having a value of 0.001 UF and attached to electronic ground conductive line E which is connected to −5 VDC giving the signal a DC voltage appearance. The signal leaving the halfwave rectifier HWR1 travels along conductive line 4 across capacitor C2 having a value of 0.01 UF, then across a 100k OHM resistor R1 which splits into two conductive lines, namely 6 and 8. Line 6 enters into the quad amplifters/buffers (intergrated circuit 1) at connection pin 3 which is used as amplifiers, buffers, triangle/square wave generators, voltage regulators and a non-inverting/inverting amplifier for amplifications and rejuvenation. Line 8 connects to a 5 MEGA-OHM variable resistor (R2 set a 1 MEGA OHM) and then to the output of intergrated circuit 1 at pin connection 4, the joining of this signal on line 8 with a signal from pin 4 creates a newer waveform. This newer waveform that now appears on line 10 is more of a straight DC voltage signal with small wave shapes appearing on it as shown in FIG. 1A, signal no. 2. New signal 2 leaves intergrated circuit 1 along line 10 and enters (a dual retriggerable monostable multivibrators with clear) intergrated circuit 2 at pin connection 2. Intergrated circuit 2 performs a signal convertion and amplification to increase the signal to a high voltage signal and converts said signal to a square wave signal no. 3. Said square wave leaves intergrated circuit 2 at pin connection 13 on conductive line 12 and enters intergrated circuit 3 at pin connection 2. Said intergrated circuit 3 is a quad two (2) input positive nor gate (both positive (+) and negative (−) logic could be used), which is designed in a latching operation for triggering. When said square wave signal no. 3 is generated from intergrated circuit 2 and enters intergrated circuit 3, said intergrated circuit 3 generates a high signal on pin connection 4 (signal no. 4). Said new high signal then travels via conductive line 14 through and across another 50K OHM variable resistor (R5 which is set at 19K OHM) and enters the base position (B) on a NPN transistor T1 (Darlington TIP 120/125) which amplifies the voltage and the current for further usage. Said signal now leaves transistor T1 by way of the collector C on conductive line 16 and travels across diode D3 and enters relay RR1 (SPDT coil 5 VDC contacts, subminiature PC relay, resistance 56 OHM, current 9 MA, 1 AMP at 125 VAC) on conductive line 18 and 18a, when the signal is present from the transistor, it triggers said relay RR1 to latch a connection from the normal state (pin 5 to pin 3) to a new state (pin 5 to pin 4) which creates a voltage connection, thereby, triggering the alarm unit. The connection to which the relay RR1 is connected to the alarm unit is from relay pin connection 5 to conductive line 20 and conductive line 20a. Conductive line 22 is attached to relay RR1 at pin connection 4 (normally open when the signal is not present on lines 18 and 18a) with the other end of conductive line 22 connected to conductive line 22a on the positive (+) side of a 12 volt DC power supply.

Intergrated circuit 3 is connected at pin 7 by conductive line 50 and 50a to a reset button RB1 which takes the high signal which has been generated due to detection of a break or damaged area in the cable and when said reset button is pushed, it puts a low signal to intergrated circuit 3 at pin connection 6 by conductive line 54, clearing the alarm (turning the alarm off).

All information for the internal circuitry are located in reference books stated below: Texas Instruments, TTL Databook for Engineers 2nd edition (LCC4112 74062-116-A1); National Semiconductor Corp., Linear Databook 1980 edition (IM-RRD85M31).

Power supply arrangements:

Negative (−) 5 volts direct current (VDC) is connected to various positions on the instant invention. The −5 VDC side of the 5 volt power supply is connected to conductive line E by conductive line 66. The −5 VDC is connected to the capacitor C1 on the electronic ground side E which has magnetic sensing device 12 ground side electronically coupled to it. Leaving connection E and 66 (where E and 66 are connected together) is conductive line 28 which connects said lines E and 66 (which have −5 VDC present) to conductive line 28 which is connected to conductive lines 30, 32 and 32a. The −5 VDC is connected to intergrated circuit 1 at pin connection 7 by conductive line 30 and to intergrated circuit 2 by conductive line 32 which then splits into two conductive lines, 34 terminating at pin connector 8 of intergrated circuit 2 and 36 which then also splits into two conductive lines, 38 terminating at pin connector 1 of intergrated circuit 2 and 40 terminating at capacitor C3 (having a value of 2 UF at 6 V) which then terminates at intergrated circuit 2 at pin connection 14 by conductive line 42.

Intergrated circuit 3 connects to −5 VDC by conductive line 32a terminating at pin 7. Exiting from intergrated circuit 3 at pin 7 is conductive line 50 and splits into two conductive lines, 52 which terminates on the emitter of T1 and 50a terminating on one side of the reset button RB1 with said transistor T1 connected to the −5 VDC on the emitter E side by conductive line 52.

INTERGRATED CIRCUIT 1

The positive (+) 5 VDC is connected to two points on intergrated circuit 1. One connection is by conductive line 70 to a 5 MEGA-OHM variable resistor (R3 set at 2 MEGA-OHM and said current leaves said variable resistor R3 by conductive line 70a and enters the input on intergrated circuit 1 at pin connection 2. The other +5 VDC is connected to conductive line 72 which is connected to said intergrated circuit 1 at connection 14 to supply power to said intergrated circuit 1 so that it can become operational. Said +5 VDC is also connected to intergrated circuit 3 at pin connection 14 by conductive line 74 and 74a by conductive line 68 and also is connected to relay RR1 at pin connection 2 of said relay by conductive line 18a with the diode D3 connected across relay RR1 at pin 1 and 2 of said relay RR1.

INTERGRATED CIRCUIT 2

The output of intergrated circuit 1 is connected at pin 4 of intergrated circuit 1 by conductive line 10 to the input of intergrated circuit 2 at pin connection 2. The +5 VDC is connected to intergrated circuit 2 in various ways. The +5 VDC is connected by conductive line 44 to pin connection 3 on intergrated circuit 2 for clear purposes when intergrated circuit 2 is activated. The +5 VDC is also connected by conductive line 80 which splits into two conductive lines 80a and 82. Conductive line 82 connects to intergrated circuit 2 at pin connection 16 and supplies power for operational use to said intergrated circuit 2. Conductive line 80a enters 500 K-OHM variable resistor (R4 that is set at 22K OHMS) in conjunction with capacitor C3 which connects to pin 15 of intergrated circuit 2 by conductive line 84. The output of intergrated circuit 2 at pin connection 4 on conductive line 12a is not used at this time but is available for future implementations of computerized networks or portable units.

INTERGRATED CIRCUIT 3

The output of intergrated circuit 2 is connected to the input of intergrated circuit 3 by conductive line 12. The gates in intergrated circuit 3 are set up in a latching configuration so the signal coming from intergrated circuit 2 will trigger a high output. Said intergrated circuit 3 latching configuration is set so that conductive line 60 is connected from intergrated circuit 3 at pin connection 3 to intergrated circuit 3 at pin connection 4. Conductive line 62 connects pin 1 to pin 5 of intergrated circuit 3 and conductive line 64 is provided for future implementations (i.e. portable units and computerized networks). The reset button attached to −5 VDC will trigger (when activated) a low signal to the latching circuit in intergrated circuit 3, so the high signal may be reset. The high signal from the output of intergrated circuit 3 at pin connection 4 on conductive line 14 passes through and across 50 K-OHM variable resistor (R5 set at 19K OHM) and will then become a low signal, thereby, being able to turn off an alarm which would have been generated, if a high signal would have been sent.

The output signal from intergrated circuit 3 is connected to variable resistor R5 which in turn is connected to transistor T1 which amplifies the signal to specifications of T1 and then the said signal travels across to diode D3 and enters relay RR1. The +5 VDC is connected to pin 14 of intergrated circuit 3 by conductive line 74 for powering said circuit. The +5 VDC is also connected to diode D3 by conductive line 74a so the +5 VDC is restricted from entering the transistor by using reverse-biasing of diode D3. Diode D3 is connected to two (2) parts of relay RR1. Relay RR1 is connected to the alarm unit by 2 connections. One connection pin 4 is connected to the positive (+) side of a 12 volt DC power supply by conductive lines 22 and 22a. The other connection from the relay RR1 pin connection 5 is by conductive line 20 and 20a which is connected to one side of sonar alert speaker S1. The opposite side S2 of said sonar alert unit connects by conductive line 92 to an on/off switch (DPDT) and is normally in the off position. Extending from the sonar alert speaker S1-side is another connection going from S1 to a minor alarm MIN-1 (in a lamp connection arrangement) by conductive line 94. Leaving said minor alarm MIN-1 on conductive line 96 enters a major alarm MAJ-1 (also a lamp arrangement connection). Leaving the major alarm MAJ-1 on conductive line 98 it joins together on conductive line 90. Conductive line 90 extends from the −12 VDC side of the power supply to the on position of the on/off switch SW1. Also extending off of conductive line 90 is another line, conductive line 100 which connects to the minor alarm (MIN-1). Both conductive lines 98 and 100 are connected to a test point by conductive line 102 which is connected to another side of the on/off switch (SW1) used in testing to see if the lights (lamps) are in working order.

The cable depending upon the thickness (size of cable, or its gauge) has to be set at different distances from the magnetic sensing device. Example, a small cable size in thickness (approximately ⅛" in diameter) must be set approximately 1"–1½" away, while the thicker cable (1" in diameter) must be set 11"–12" (approximately) away. This is due to the stronger lines of flux (magnetism) that the cable holds. The bigger the cable the more magnetism occurs creating a high density of magnetic lines of flux.

While the form of the apparatus herein described constitutes a preferred embodiment of the invention, it is understood that the invention is not limited to this precise form of apparatus and that changes may be made therein without departing from the scope of this invention.

Having regard to the foregoing disclosure I claim the following as the patentable embodiments thereof:

1. Apparatus to detect a flaw in a moving cable that can be magnetized, comprising:

(a) first and second magnets each having a north pole and a south pole spatially separated and adjacent said cable to magnetize the moving cable;

(b) a magnetic sensing device adjacent said cable located between said magnets independent of and not coupled to either of said magnets wherein the moving cable in either direction after being magnetized by one of said magnets is passed through the magnetic sensing area of said magnetic sensing device, said magnetic sensing device sensing any change in the magnetic field of the magnetized cable, said change in the magnetic field resulting from any flow in said magnetized cable; and (c) means to convert the output of the magnetic sensing device to useable form so that the flaw of the magnetic cable becomes known.

2. Apparatus to detect a flaw in a moving cable that can be magnetized, as recited in claim 1, in which the means to convert the output of the magnetic sensing device to a useable form is an alarm unit that will activate when a flaw is present.

3. Apparatus to detect a flaw in a moving cable that can be magnetized, as recited in claim 1, in which the magnetic sensing device comprises a gauss meter which will detect a change in the magnetic field of a magnetized cable that passes through said device, said change arising in the magnetic field due to a fault in the magnetic cable that passes through said device.

4. Apparatus to detect a flaw in a moving cable that can be magnetized, as recited in claim 1, in which the output of the magnetic sensing device is a sine wave having spikes, said spikes on said sine wave increasing when a fault in a magnetized cable is detected.

5. Apparatus to detect a flaw in a moving cable that can be magnetized, comprising:

(a) first and second magnets each having a north pole and a south pole positioned spatially apart with respect to said moving cable so as to magnetize a portion of said cable as it passes by in either direction;

(b) gauss meter means located between and independent of and not coupled to either of said magnets to sense the magnetization of said cable after the latter leaves the magnetic field of one of said magnets producing a sine wave containing spikes, said spikes on said sine wave increasing when a fault in said magnetized cable is detected; and (c) means responsive to the spiked output of said gauss meter means indicating the presence of a fault in said cable to produce an alarm.

* * * * *